United States Patent [19]

Henriksen et al.

[11] Patent Number: 4,930,512

[45] Date of Patent: Jun. 5, 1990

[54] HAND HELD SPRING-LOADED ULTRASONIC PROBE

[75] Inventors: William Henriksen, Hauppauge; Louis Katz, Flushing; David G. Wuchinich, New York, all of N.Y.

[73] Assignee: Sonomed, Inc., Lake Success, N.Y.

[21] Appl. No.: 207,675

[22] Filed: Jun. 16, 1988

[51] Int. Cl.⁵ .............................................. A61B 8/10
[52] U.S. Cl. .............................................. 128/661.06
[58] Field of Search ................................. 128/645–652, 128/745, 661.06; 604/22

[56] References Cited

U.S. PATENT DOCUMENTS

| | | | |
|---|---|---|---|
| 2,763,153 | 4/1954 | Simjian | 73/678 |
| 2,882,891 | 6/1957 | Husted | 128/2 |
| 2,984,099 | 5/1961 | Tolman | 128/646 |
| 3,376,735 | 9/1964 | Garber et al. | 73/80 |
| 3,390,572 | 4/1965 | Murr | 73/80 |
| 3,453,998 | 7/1969 | Giglio | 128/745 |
| 3,614,890 | 11/1968 | Bates | 73/71.5 |
| 3,810,459 | 5/1974 | Becker | 128/662.04 |
| 3,835,836 | 9/1974 | Kanter et al. | 128/2 T |
| 3,934,462 | 1/1976 | Rende | 73/80 |
| 3,992,926 | 11/1976 | Berryhill | 73/80 |
| 4,122,837 | 10/1978 | Leonard | 128/2 S |
| 4,122,838 | 10/1978 | Leonard | 128/2 S |
| 4,141,346 | 2/1979 | Dean, Jr. et al. | 128/2 T |
| 4,151,834 | 5/1979 | Sato et al. | 128/660 |
| 4,154,114 | 5/1979 | Katz et al. | 73/629 |
| 4,165,736 | 8/1979 | Wolfson | 128/687 |
| 4,166,395 | 9/1979 | Dannehl | 73/634 |
| 4,213,464 | 7/1980 | Katz et al. | 128/645 |
| 4,257,687 | 3/1981 | Kohayakawa | 351/7 |
| 4,261,367 | 4/1981 | Freese | 128/660 |
| 4,281,662 | 8/1981 | Brent | 128/676 |
| 4,305,399 | 12/1981 | Beale | 128/645 |
| 4,437,468 | 3/1984 | Sorenson et al. | 128/660 |
| 4,484,569 | 11/1984 | Driller et al. | 128/661.06 X |
| 4,508,121 | 4/1985 | Myers | 128/639 |
| 4,515,583 | 5/1985 | Sorich | 604/22 |
| 4,538,618 | 9/1985 | Rosenberg et al. | 128/662.04 |
| 4,564,018 | 1/1986 | Hutchinson et al. | 128/660 |
| 4,576,176 | 3/1986 | Myers | 128/660 |

FOREIGN PATENT DOCUMENTS

| | | | |
|---|---|---|---|
| 565314 | 1/1974 | France | 128/651 |
| 5356 | of 1911 | United Kingdom | 128/651 |

OTHER PUBLICATIONS

Coleman, D., Lizzi, F., and Jack R. *Ultrasonography of the Eye and Orbit* Lea & Febiger 1977.

Primary Examiner—Francis Jaworski
Attorney, Agent, or Firm—Pennie & Edmonds

[57] ABSTRACT

An apparatus is disclosed for uniformly biasing a transducer against a human eye comprising an outer housing, an inner housing insertable into the outer housing and a biasing means. The inner housing has attached thereto a transducer and is movable with respect to the outer housing between an extended position and a retracted position. Bushing means are provided between the respective housings to maintain such housings in a concentric relationship and also to reduce friction between the respective housings. The probe is adapted to be applied against an eye and maintain substantially constant pressure on the eye, hand motion being compensated for by the biasing means, illustratively a spring.

40 Claims, 5 Drawing Sheets

HAND HELD SPRING-LOADED ULTRASONIC PROBE

TECHNICAL FIELD

The present invention relates generally to a device for measuring distances between certain elements of a human body and more particularly to a spring-loaded hand held ultrasonic probe for accurately measuring an axial length of the human eye even under conditions of erratic hand movements.

BACKGROUND OF THE INVENTION

The use of high frequency ultrasonic waves for obtaining information from objects is well known. For example, high frequency ultrasonic waves are often used in the medical field to obtain information relating to internal elements, organs and the structure of living bodies.

Ultrasonic wave transmission is particularly useful in determining the distance between various elements and organs in living bodies, and especially in determining distances between various elements of the human eye.

One of the most useful applications of ultrasonic wave transmission is a measure of the axial length of the eye, i.e., the measure of the distance from the cornea to the retinal surface. This distance allows an ophthamologist to compute a refractive power of the eye be well known methods and then to specify the correct intraocular lens for patients undergoing, for example, cataract surgery. In fact, although optical methods for measuring this axial distance are known, the ultrasonic wave transmission method is the method of choice for making axial length measurements in patients whose cataracts prevent sufficient transmission of light to the retina.

The technology and technique for making measurements in ophthalmology, including determination of the axial length of the human eye by utilizing ultrasonic wave transmission is disclosed in Coleman, D., *Ultrasonography of the Eye and Orbit*, Lea & Febiger (1977). In an illustrative method of making such measurement, referred to in the art as "Ultrasonic A-Scan", a hand held probe-like device is placed in contact with a cornea of the human eye. The probe-like device comprises a transducer assembly and a separate fixation light which the patient is instructed to view. As the patient views the fixation light, high frequency ultrasonic waves, preferably of very short duration, are transmitted by a transmitter of the transducer assembly into the eye. These high frequency ultrasonic waves are reflected from various anatomical structures within the eye. More specifically, a first reflection occurs at an anterior corneal surface of the eye and a last reflection occurs at a retinal surface of the eye. Intermediate reflections include a second reflection at a posterior corneal surface, a third reflection at an anterior lens surface and a fourth reflection at a posterior lens surface.

These five reflected ultrasonic waves, or echoes, are sensed by an ultrasonic transducer assembly in the probe and converted to electrical impulses which are displayed on a display device. If the velocity at which the waves travel through the anatomical structures of the eye is known, the difference in time taken for two successive echoes from different structures within the eye to reach the transducer is a measure of the physical distance between these structures. The sound velocity of the eye and its anatomical structures has been very carefully measured and are well known.

A description of a known transducer assembly may be found in U.S. Pat. No. 4,213,464 to Katz et al., while a description of a known biometric measuring device may be found in U.S. Pat. No. 4,154,114 to Katz et al. Each of these two U.S. patents are expressly incorporated herein by reference. U.S. Pat. Nos. 4,508,121 to Myers, 4,564,018 to Hutchison et al. and 4,576,176 to Myers further disclose ocular measurement devices and are also incorporated herein by reference.

The measured physical distances between various structures of the eye is accurate only to the extent that the eye is not deformed when such measurements are made. Should the eye structure be deformed during the measurement process, any resulting measured distances will not be representative of actual distances and will lead to replacement lenses of improper refractive power, thereby depriving a patient of full use of his vision.

Unfortunately, known devices in attempting to measure distances between various anatomical structures of the eye introduce a deforming force to the eye and thereby result in inaccurate measurements. For example, in measuring an axial length of the eye, known ultrasonic transducers are placed upon and forcefully held in contact with the anterior surface of the cornea. In use of such known transducers, especially transducers of the hand held variety, any hand movement will result in a change of pressure applied to the eye by the transducer assembly of the probe-like device. Should such pressure exceed the pressure exerted by the fluids within the eye and the eye structure itself, the corneal surface may be deformed. Under typical conditions the pressure of the fluids within the eye has been found to be approximately 14 mm Hg.

Measurements of axial lengths taken under these conditions using the ultrasonic wave transmission method will produce an error since the cornea and possibly other structures of the eye are inadvertently slightly flattened due to pressure applied by the transducer assembly. The flattening is called applanation and represents the chief source of error in ultrasonic A-Scan measurements.

Since the ultrasonic probe-like device is a rigid structure, is typically hand held and the pressures within the eye are small compared to those that the human hand can produce in even a soft application of the probe to the eye, it is extremely difficult to remove applanation errors in ultrasonic A-Scan measurements. If a non-distorting contact between the probe and the cornea could be ensured, it is believed that axial length measurements could be made to within 0.01 mm. This would represent an increase of an entire order of magnitude in accuracy over properly used ultrasonic A-Scan systems which are capable of measuring distances to within 0.1 mm.

SUMMARY OF THE INVENTION

The present invention relates to a device for uniformly biasing a transducer assembly against a human eye and comprises an outer housing adapted to be hand held and an inner housing slidably insertable into the outer housing and movable between an extended position for contact with the eye and a retracted position with respect to the outer housing for protective storage thereof. The device includes means for biasing the inner housing into the extended position and means for holding the transducer. The holding means and the transducer are provided on a front portion of the inner housing for emitting and receiving ultrasonic energy to/from the eye when the inner housing is in its extended position. The ultrasonic energy is preferably in the form of ultrasonic waves and may directly enter the eye or may first pass through a water stand-off before entering the eye. The biasing means is adapted to provide reduced biasing forces when the eye is contacted to avoid applanation thereof.

The biasing means preferably comprises a spring which has associated therewith a spring constant, the spring constant being essentially the same in the extended position and in the retracted position.

The device also includes illumination means concentrically mounted within the front portion of the inner housing rearward of the holding means. The illumination means is viewable by the eye and preferably comprises a fixation light such as an LED and a fiber optic rod. A curved contact member is attached to the transducer for conforming contact with the eye. Alternatively, the transducer may be supplied with a curved surface for sensing of the sound beam on the retina and for conforming contact with the eye. The contact member or curved surface and the transducer are each provided with a concentric bore therethrough so as to enable the eye to view the illumination means. Additionally, the transducer generally has associated therewith a focusing means such as a lens for providing a properly focused beam.

The device preferably includes an echo ranging device electrically connected to the transducer for calculating intraocular distances. The echo ranging device may include a display for graphically depicting such intraocular distances.

The device preferably includes means for limiting travel of the inner housing between the extended position and the retracted position. Such limiting means preferably comprises an end stop attached to the inner housing for contacting a first end of the spring and an end plug attached to the outer housing for contacting a second end of the spring. The end plug is adjustably and removably attached to the outer housing so as to permit removal or replacement of the spring. Preferably, the end plug is adjustable by varying its length of insertion into the outer housing so as to facilitate selecting and/or adjusting an initial preload.

The device preferably includes a plurality of bushings attached to an inner surface of the outer housing for maintaining the inserted inner housing in a concentric relationship with the outer housing and providing a low friction interface between the inner and outer housings. The bushings may be linear ball bushings which are preferably held in place by set screw means.

The device and in particular, the transducer, may directly contact the eye. Alternatively, a water stand-off attached to a front portion of the inner housing may be provided to contact the eye. The water stand-off may comprise a stand-off section, a membrane for conforming to the eye and a seal means such as an O-ring to seal the membrane to the stand-off section.

The invention also relates to a device for biasing a transducer against an eye with a predetermined pressure not exceeding a threshold pressure which would cause deformation of the eye. This device comprises an annular shaped transducer which has a contact surface to matingly engage the eye, an inner housing member, a fixation light, first lead means, second lead means, an outer housing, bushing means, limiting means and spring means.

The inner housing member is concentrically attached to the transducer and has a rear portion and a front portion, the front portion being greater in diameter than the rear portion and being provided with a tip section having a bore extending therethrough. The fixation light is mounted concentrically within the tip section of the inner housing member at a rear end of the bore which extends through the tip section. The bore extends outwards through a center of the annular shaped transducer. The first lead means is provided for transmission of electrical signals and is connected to the fixation light and extends rearward through a center bore in the inner housing and exits a rear portion of the inner housing. The second lead means is provided for transmission of electrical signals and is connected to the transducer and extends rearward through the center bore in the inner housing and exits the rear portion of the inner housing. The outer housing is provided with a front portion and a rear portion. The inner housing is at least partially concentrically insertable into the outer housing. The bushing means provides a low friction interface between the inner and outer housings and maintains the inner housing in a concentric relationship with the outer housing. The bushing means preferably comprises a plurality of linear ball bushings and is attached to an inner surface of the outer housing. The limiting means is provided for limiting the movement of the inner housing relative to the outer housing between the extended position and the retracted position. The spring means biases the inner housing into the extended position with respect to the outer housing. The inner housing is positionable between the extended and retracted positions and the spring means has a spring constant which is the same in the retracted and the extended position of the spring. The spring means is positioned with respect to the limiting means such that the pressure applied by the transducer to the eye does not exceed the threshold pressure which would cause deformation of the eye. At least a portion of the limiting means is adjustably and removably attached to the outer housing so as to permit removal of the spring and also to permit selection and adjustment of a preload force.

The present invention also relates to an improvement in a diagnostic device for measuring distances between anatomical structures. Such a diagnostic device is provided with a transducer assembly for contacting an anatomical surface, transducer holding means for holding the transducer and lead means connected to the transducer for transmission of electrical signals. The improvement comprises biasing means and second holding means, the transducer holding means being insertable into the second holding means and movable therein between an extended position and a retracted position. The biasing means biases the transducer holding means in relation to the second holding means such that the transducer holding means is in the extended position at rest and at least partially in the retracted position upon forceful engagement of said device with an eye. The biasing means provides biasing forces which are less than that which would cause deformation of the eye.

This diagnostic device includes means for limiting travel of the second holding means with respect to the transducer holding means. Such travel is limited between the extended position and the retracted position.

Preferably, the biasing means comprises a spring which has associated therewith a spring constant which is essentially the same in the extended position and in the retracted position.

The means for limiting travel preferably comprises an end stop which is attached to the transducer holding means and which contacts a first end of the spring. The means for limiting travel further comprises an end plug which is attached to the second holding means and which contacts a second end of the spring. The end plug is removably attached to the second holding means so as to permit removal or replacement of the spring.

The diagnostic device further comprises a plurality of bushings attached to an inner surface of the second holding means. These bushings maintain the inserted transducer holding means in a concentric relationship with the second holding means and also provides a low friction interface between the transducer holding means and the second holding means. The bushings may be linear ball bushings.

The device and in particular, the transducer, may directly contact the eye. Alternatively, a water stand-off attached to a front portion of the inner housing may be provided to contact the eye. The water stand-off may comprise a stand-off section, a membrane for conforming to the eye and a seal means such as an O-ring to seal the membrane and the stand-off section.

The present invention also relates to a device for uniformly biasing a transducer against a human eye comprising an outer housing adapted to be hand held, an inner housing slidably insertable into the outer housing and movable between an extended position for contact with the eye and a retracted position with respect to the outer housing for protective storage thereof, spring means, limiting means and holding means.

The spring means biases the inner housing into the extended position and has associated therewith a spring constant which is essentially the same in the extended position and in the retracted position. The limiting means is for limiting travel of the inner housing between the extended position and the retracted position and includes an end stop attached to the inner housing for contacting a first end of the spring means and an end plug attached to the outer housing for contacting a second end of the spring means, wherein the end plug is adjustably and removably attached to the outer housing so as to permit removal or replacement of the spring means and selection and adjustment of a preload force. The holding means holds a transducer and is provided on a front portion of the inner housing for engaging the eye when the inner housing is in the extended position. The spring biasing means is adapted to provide reduced biasing forces when the eye is contacted to avoid applanation thereof.

Illumination means viewable by the eye is preferably provided and is concentrically mounted within the front portion of the inner housing rearward of the holding means. A curved contact member is preferably provided and is attached to the transducer for conforming contact with the eye. Alternatively, the transducer may be provided with a curved surface for conforming contact with the eye. The curved contact member or curved surface and the transducer are each provided with a concentric bore therethrough so as to enable the eye to view the illumination means.

The device preferably includes an echo ranging device electrically connected to the transducer for calculating intraocular distances. The echo ranging device may include a display for graphically depicting such intraocular distances.

The device includes a plurality of bushings which are attached to an inner surface of the outer housing for maintaining the inserted inner housing in a concentric relationship with the outer housing and providing a low friction interface between the inner and outer housings. The bushings may be linear ball bushings.

BRIEF DESCRIPTION OF THE DRAWINGS

Preferred embodiments of the invention are shown herein with reference to the drawing FIGS. in which similar elements are labelled similarly and wherein.

DETAILED DESCRIPTION OF THE PREFERRED EMBODIMENTS

Figure 1:
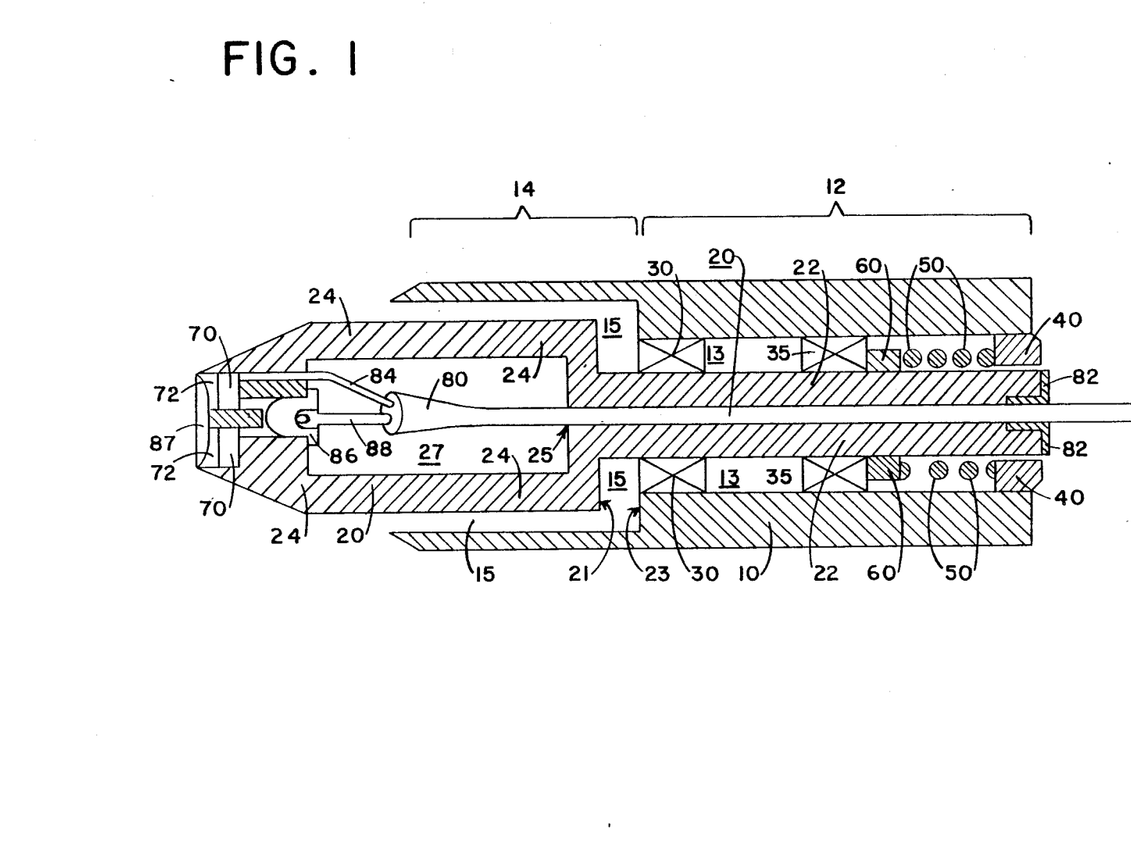
FIG. 1 is a cross section of a first embodiment of a hand held probe of the present invention for direct contact with an eye.

Referring initially to FIG. 1 which is not necessarily drawn to scale there is illustrated a cross section of a hand held probe of the present invention for direct contact with an eye comprising an outer housing 10, an inner housing 20, and bushings 30, 35. Spring retaining plug 40, spring 50 and end stop 60 are preferably provided for suitable biasing between outer housing 10 and inner housing 20. Transducer 70 is provided at a front end of inner housing 20.

Outer housing 10 is an elongated cylindrical tubular member having a rear portion 12 defining a rear cylindrical chamber 13 and a front portion 14 defining a front cylindrical chamber 15. Outer housing 10 is adapted to be hand held.

Inner housing 20 is an elongated cylindrical member having a rear portion 22 and a front portion 24. Inner housing rear portion 22 is adapted to be inserted into outer housing rear portion 12 while inner housing front portion 24 is adapted to be inserted into outer housing front portion 14. Inner housing 20 is provided with a chamber 27 within front portion 24 and a bore 25 through rear portion 22 for accommodating a cable 80. A rear end of bore 25 has inserted therein a flexible bushing 82 to serve as a strain relief for cable 80.

Transducer 70 is inserted into a frontal tip section of front portion 24 of inner housing 20 which is adapted to receive such transducer. Transducer 70 illustratively is employed for both transmitting and receiving the ultrasonic waves. Transducer 70 is preferably annular in shape with a bore therethrough, such bore extending through the frontal tip section of inner housing 20 into chamber 27. Transducer 70 is attached to wires 84 which form part of cable 80. A contact member 72 is attached to transducer 70. Contact member 72 is provided with a concave tip for conforming to and placement directly upon the eye.

Since it is desired that inner housing 20 and transducer 70 move with respect to outer housing 10 with as little friction as possible and since a patient has a tendency to not remain absolutely still and since it is generally desired that transducer 70 and inner housing 20 track the eye and maintain a constant pre-determined pressure upon the eye, inner housing 20 and transducer 70 as well as any other elements attached to housing 20 or transducer 70 preferably have a low mass. Furthermore, housings 10,20 may each comprise one or more sections so as to facilitate assembly and/or manufacture. Such sections may be fastened by any suitable means such as a threaded connection.

Fixation light 86 is centered at a front end of chamber 27 and is visible to a patient upon whose eye the present invention in placed. The patient views the light by way of the bore through preferably annular shaped transducer 70 and also by way of fiber optic rod 87, such bore extending into chamber 27. Fixation light 86 is preferably a light emitting diode (LED) and is attached to wires 88 which form part of cable 80. Alternatively, a combination fixation light and transducer assembly in which the fixation light is an integral part of the transducer may be employed.

Bushings 30,35 provide the means by which inner housing 20 is slidably inserted into outer housing 10. Although two bushings are depicted in FIG. 1, any suitable number and any suitable means which provide for relative axial movement between outer housing 10 and inner housing 20 may be employed. Preferably, such means provide a minimum amount of friction between inner housing 20 and outer housing 10. It will be appreciated that bushings 30,35 may take on a wide variety of forms such as, illustratively, ball bearings. Bushings 30,35 are preferably firmly attached to outer housing 10 and are in slidable contact with inner housing 20. Bushings 30,35 may each comprise a single annular element having ball bearings arranged in an annular fashion around the inner housing. In a preferred embodiment, bushings 30,35 each comprises three separate ball circuits. Each linear ball circuit comprises an oblong loop of recirculating balls, with the balls of one section of the loop in contact with the inner housing in an axial direction. These three ball circuits are spaced 120' apart from each other.

A bushing which has been found to be suitable is model INST-369-SS available from Thomson Industries of New York. Advantageously, such bushing introduces a minimum amount of static friction which must be overcome for the device to operate properly and thus aids in preventing applanation of the cornea. The bushing may be held in place by a set screw or by elastomeric O-rings. Removal of the busing and subsequent disassembly of the entire probe is thus easily accomplished.

End stop 60 is firmly attached to rear portion 22 of inner housing 20 and serves to limit the extended position of inner housing 20 relative to outer housing 10. In the fully extended position, end stop 60 contacts bushing 35. As inner housing 20 is retracted into outer housing 10, end stop 60 moves away from bushing 35 until a fully retracted position is reached. The fully retracted position is reached when rear face 21 of inner housing front portion 24 contacts front face 23 of outer housing rear portion 12 and/or bushing 30. End stop 60 may take on a variety of forms and illustratively comprises an annular ring tightly surrounding inner housing rear portion 22.

End plug 40 is attached to a rear end of outer housing rear portion 12 and serves as a stop against which an end of spring 50 is positioned. The other end of spring 50 is positioned against end stop 60. Thus, spring 50 serves as a biasing means to bias inner housing 20 away from outer housing 10, i.e., to bias the present invention into an extended position. End plug 40 is preferably removable and adjustable, either by frictional engagement/disengagement or a threadable connection or any of a variety of known removable fastening techniques.

Advantageously, spring 50 is chosen to have a spring constant such that placement of the transducer against a patient's eye and subsequent retraction of the inner housing into the outer housing will provide a force exerted by the present invention on the eye, such force advantageously not producing any significant deformation of the eye and more particularly of the cornea. Furthermore, the spring length is selected such that even when the probe is fully retracted the pressure applied by the probe against an eye is less than the threshold pressure below which deformation will not occur. An illustrative amount of travel of the inner housing within the outer housing is one-quarter inch. Illustrative spring constants are 1-2 gm/mm.

Spring 50 thus accommodates erratic hand movements without producing pressures at the cornea or otherwise within the eye exceeding a threshold level beyond which deformation will occur, thereby permitting an accurate measurement of axial distances and especially of the distance from the cornea to the retina.

Of course, compliance of the hand held probe of the present invention will vary with the angle of presentation to the eye, becoming less compliant as the probe is given a slightly vertical orientation and the weight of the transducer assembly itself produces an additional pressure upon the eye and more compliant for an angle of presentation that places part of the transducer assembly weight upon the spring. Fortunately, typical axial length measurements and the like are invariably done in a horizontal position which minimizes these gravitational effects.

For situations in which the patient assumes a supine, i.e., face upward, position the weight of the transducer and inner housing of the vertically held spring-loaded probe will exert an additional force on the eye. In this situation, however, a spring having a spring constant and/or length to support the weight of the inner housing components and to offset or counteract gravitational forces thereupon should be used. If the weight of such inner housing and transducer is too great to be compensated by adjusting the spring constant and/or length, re-positioning of the spring so as to tend to retract the inner housing will counteract such gravitational force. Similarly, should the patient be looking downward, a spring having an increased spring constant and/or length may be employed to exert additional force to overcome the gravitational force exerted by the inner housing and transducer.

Figure 2:
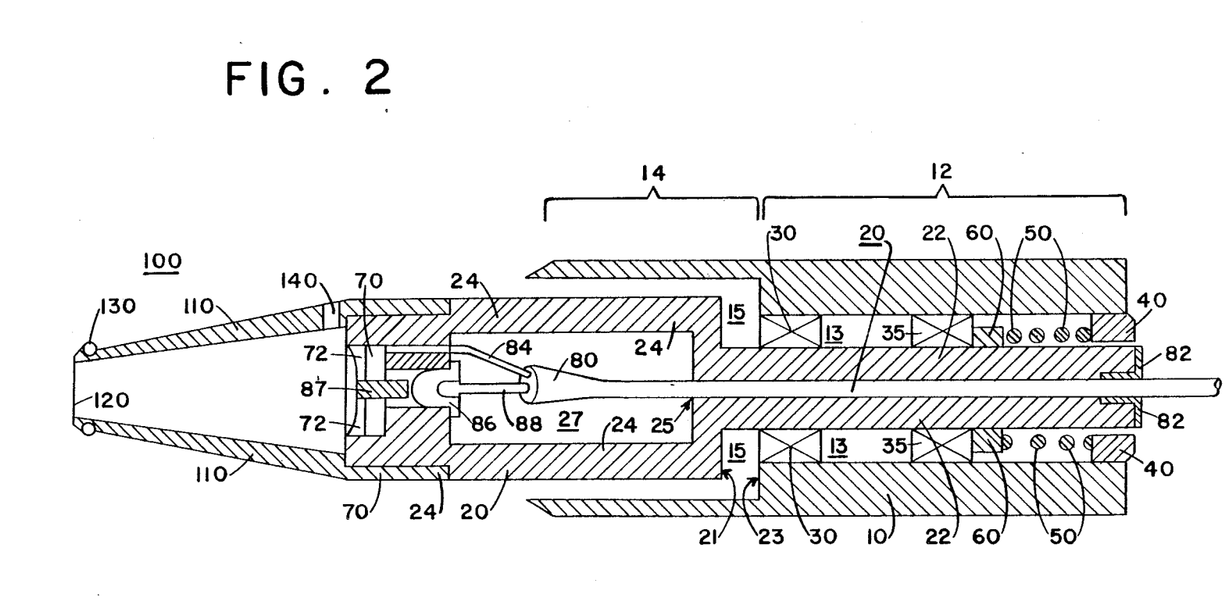
FIG. 2 is a cross section of a second embodiment of a hand held probe of the present invention having a water stand-off for contact with the eye.

Referring now to FIG. 2, there is depicted a second embodiment of the invention in which a water stand-off 100 is employed for contacting the eye. Water stand-off 100 comprises a stand-off section 110, a membrane 120, a water seal 130 and a water-fill hole 140.

The probe depicted in FIG. 2 is identical to the probe depicted in FIG. 1 except for water stand-off 100 and a reduced diameter of inner housing front portion 24 for mating sealing contact with a rear portion of stand-off section 110. Stand-off section 110 is preferably constructed from transparent plastic.

Membrane 120 is attached to a front portion of stand-off section 110 by water seal 130 and is preferably constructed from a thin latex material. Water-fill hole 140 is provided in stand-off section 110 for introducing water into section 110. Water seal 130 preferably is an O-ring which seals membrane 120 against a front portion of stand-off section 110.

Water stand-off 100 of the probe depicted in FIG. 2 advantageously reduces the possibility of applanation, thereby permitting accurate measurements to be taken, especially of the anterior chamber of the eye. In use of this device, the membrane of the water-filled stand-off is brought into contact with an eye and conforms thereto by displacing a small quantity of water within the stand-off section. In addition, the water reservoir increases the accuracy of such measurements by causing excitation pulses from the transducer to possess a time difference in the stand-off area, which time difference can be discerned and deleted from the desired measurements.

Figure 3:
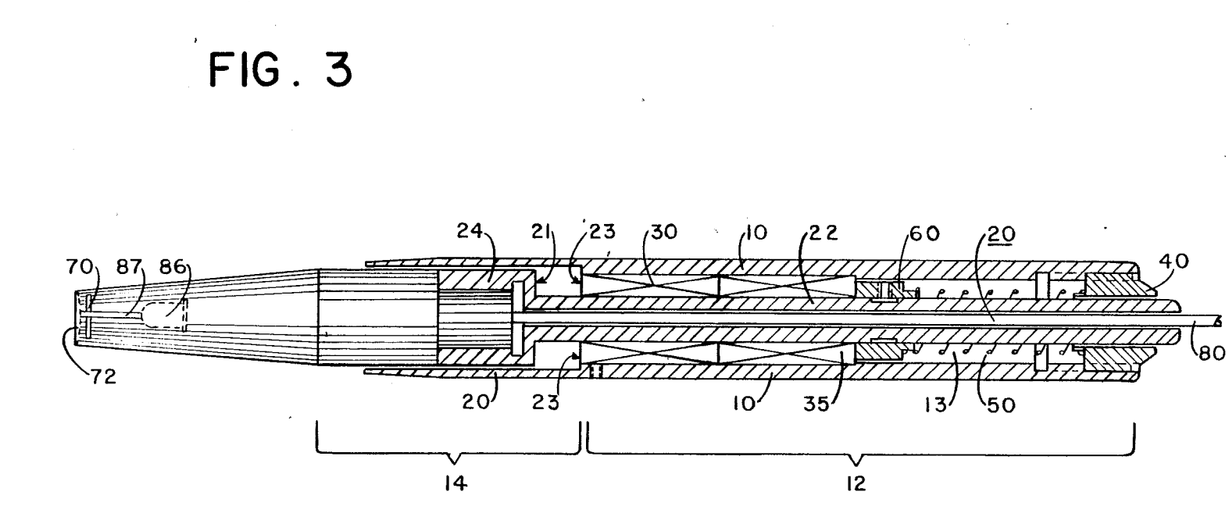
FIG. 3 is a partial cross section of a third embodiment of a hand held probe of the present invention.

Referring to FIG. 3, there is depicted a third embodiment of a hand held probe in which elements similar to corresponding elements in FIG. 1 are labelled similarly. As will be appreciated by one skilled in the art, an initial preload force may be selected by adjusting the distance which end plug 40 is inserted into outer housing 10. Additionally, a retaining set screw 90 is provided for dis-assembly of the hand held probe. Removal of set screw 90 will permit separation of bushings 30,35 from outer housing 10 and withdrawal of inner housing 20 from outer housing 10.

Figure 4:
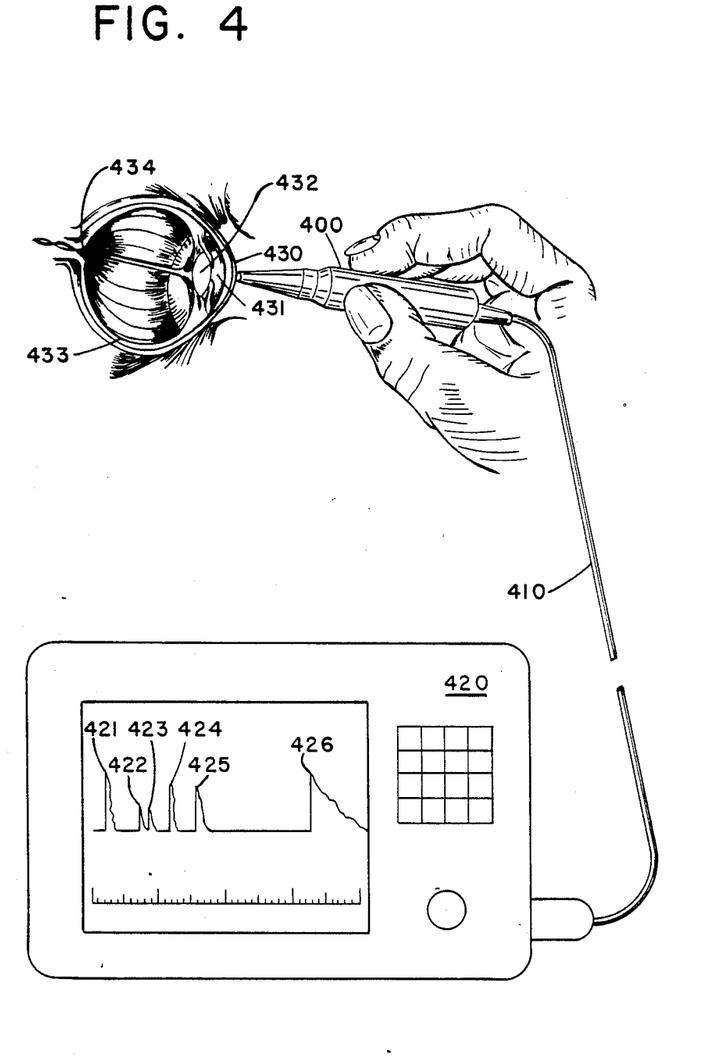
FIG. 4 is an illustration of the present invention in use and a corresponding display depicting axial lengths as measured by the hand held probe.

Referring now to FIG. 4, there is depicted the hand held probe of the present invention in use and a corresponding display depicting axial lengths. More specifically, FIG. 4 depicts the hand held spring-loaded ultrasonic probe 400 held by an operator and placed against a cornea of a patient. The probe is connected by cable 410 to echo ranging display device 420.

Display device 420 comprises a screen which graphically displays reflected signals in pulse form. The display, not necessarily drawn to scale, depicting pulses 421–426 represents a typical cycle of operation. More specifically, pulse 421 is the initial sound pulse which is emitted by probe 400 in response to energization of the probe and pulses 422–426 are reflected echo pulses. The path take by a sound pulse is through a cornea 430, an aqueous region 431, a lens 432, a vitreous region 433 and a retina 434. A first reflection occurs at an anterior surface of cornea 430 and is represented by pulse 422. A second reflection occurs at a posterior surface of cornea 430 and is represented by pulse 423. A third reflection occurs at an anterior surface of lens 432 and is represented by pulse 424. A fourth reflection occurs at a posterior surface of lens 432 and is represented by pulse 425. A fifth reflection occurs at retina 434 and is represented by pulse 426. Thus, the distance from the anterior surface of the cornea to the retina is represented by the distance between pulses 422 and 426. This distance may be visually determined by examining the pulses and corresponding scale. Additionally, an alphanumeric display (not shown) may be provided to visually display a number representing the distance between various elements of the eye.

A preferred method for selecting an appropriate spring constant is as follows. The probe is brought into contact with an air filled rubber balloon. The balloon is either pressurized or depressurized using a small, precisely controlled pump. A water manometer is connected to the balloon to measure air pressure. Starting at a predetermined pressure level, the balloon is brought into contact with the probe and moved so as to force the transducer assembly to retract. At the onset of transducer movement visual inspection is made at the surface of the balloon contact to determine if deformation occurs. The pressure in the balloon is raised using the pump until probe retraction occurs without visible deformation (pin-cushioning) of the balloon. The pressure, as measured by the manometer when this condition is established, is the contacting pressure of the probe. The spring and bearing are selected such that the pressure is below normal intraocular levels (14 mm. Hg.). Furthermore, the spring length is selected such that even when the probe is fully retracted the pressure required for deformation is below intraocular levels. This condition can be determined by further increasing the balloon pressure until pin cushioning does not occur just before full retraction.

Thus, the present invention helps to ensure that physicians and other personnel of widely different levels of manual dexterity may make precise and accurate measurements, i.e., measurements which are substantially the same in value and which are close to the true value of the distance measured. The present invention complies with typical inadvertent and uncontrollable hand movement as the probe is held in contact with a cornea of the eye and provides a heretofore unachieved precise measurement which ultimately results in, for example, an intraocular lens prescription that more exactly duplicates the refractive power of the human lens which it replaces.

Figure 5:
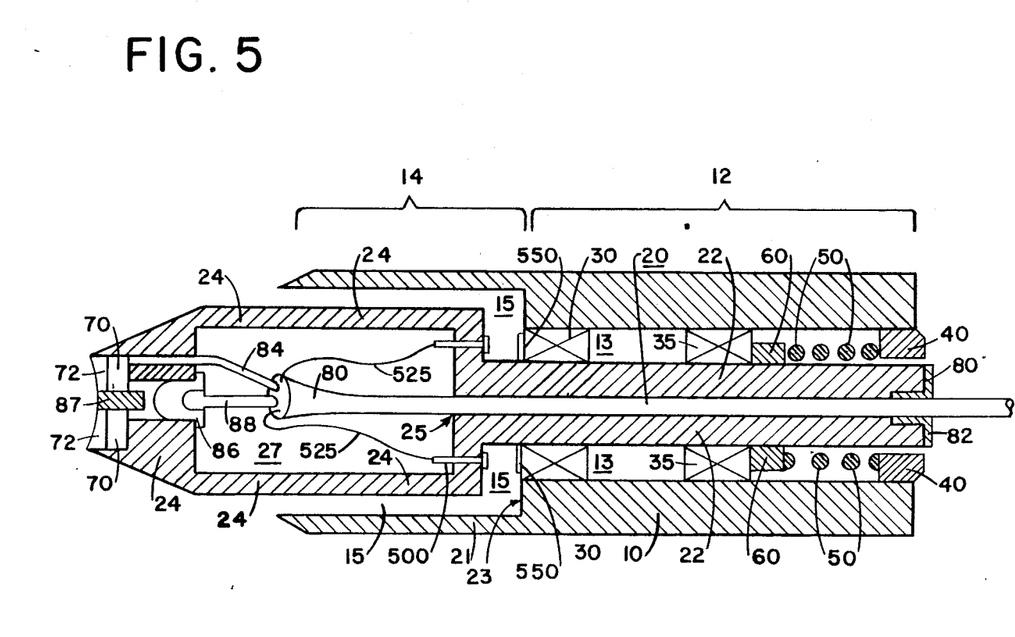
FIG. 5 is an illustration of a modification of the device of FIG. 1.

FIG. 5 illustrates another embodiment of the invention wherein the transducer of FIG. 1 includes end of travel contact pins 500, connected by leads 525 to which are included in cable 80 and connected to the system display screen. If too much force is expended by the user in applying the contact member 72 against the eye, the pins 500 contact a brass retaining ring 550 which forms part of the ball bushing assembly 30, and an electrical connection is completed. This electrical connection, which indicates the improper use of the device, can be used to short circuit the display screen, thus temporarily rendering the device inoperative. Preferably, however, an audible tone is produced to signal a possible applanation error, or a written message is generated on the system display screen, or both, to indicate that the probe is fully retracted, a situation which should be avoided to prevent obtaining erroneous readings or damage to the eye.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

More specifically, the present invention is not limited to use in ultrasonic A-scan methods or for measuring axial distances for properly selecting an intraocular lens prescription to duplicate the refractive power of the lens which it replaces, but may be used in a wide variety of other medical procedures, such as precisely measuring corneal thickness in order to make radial cuts into but not through the cornea in a medical procedure known as radial keratotomy. Although the probe has been described as hand held, the present invention may be employed in any situation in which as precise amount of pressure is required to be applied to a given object, especially under conditions of vibration and other movement. For example, the outer housing can be adapted for mounting on other apparatus used for conducting measurements on the eye.

What is claimed is:

1. A hand held apparatus for uniformly biasing a transducer assembly against a human eye comprising:
   an outer housing adapted to be hand held;
   an inner housing slidably insertable into said outer housing and movable between an extended position for contact with said eye and a retracted position with respect to said outer housing for protective storage thereof;
   means for biasing said inner housing into said extended position;
   a transducer for contacting an eye for conducting measurements thereof; and
   means for holding said transducer, said holding means and transducer being provided on a front portion of said inner housing for emitting and receiving ultrasonic energy from said eye when said inner housing is in said extended position, said biasing means providing biasing forces less than that which would cause deformation of said eye when said eye is contacted with said transducer to avoid applanation thereof while said measurements are conducted.

2. The apparatus of claim 1 further comprising illumination means concentrically mounted within said front portion of said inner housing rearward of said holding means and viewable by said eye.

3. The apparatus of claim 2 wherein said illumination means comprises a light emitting diode and a fiber optic rod.

4. The apparatus of claim 1 further comprising a curved contact member attached to said transducer for conforming contact with said eye.

5. The apparatus of claim 4 wherein said curved contact member and said transducer are each provided with a concentric bore therethrough so as to enable said eye to view said illumination means.

6. The apparatus of claim 1 further comprising an echo ranging device electrically connected to said transducer for calculating intraocular distances.

7. The apparatus of claim 1 wherein said biasing means comprises a spring.

8. The apparatus of claim 7 wherein said spring has associated therewith a spring constant, said spring constant being essentially the same in said extended position and in said retracted position.

9. The apparatus of claim 8 further comprising means for limiting travel of said inner housing between said extended position and said retracted position.

10. The apparatus of claim 9 wherein said limiting means comprises an end stop attached to said inner housing for contacting a first end of said spring.

11. The apparatus of claim 10 wherein said limiting means further comprises an end plug attached to said outer housing for contacting a second end of said spring.

12. The apparatus of claim 11 wherein said end plug is adjustably removably attached to said outer housing so as to permit removal or replacement of said spring and also to permit selection and adjustment of a preload force.

13. The apparatus of claim 1 further comprising a plurality of bushings attached to an inner surface of said outer housing for maintaining said inserted inner housing in a concentric relationship with said outer housing and providing a low friction interface between said inner and outer housings.

14. The apparatus of claim 13 wherein said bushings comprise linear ball bushings.

15. The apparatus of claim 14 further comprising set screw means for removal of said linear ball bushings.

16. The apparatus of claim 1 wherein said transducer is provided with a focusing means for producing a focused beam.

17. The apparatus of claim 1 further comprising a water stand-off attached to said front portion of said inner housing.

18. The apparatus of claim 17 wherein said water stand-off comprises a stand-off section, a membrane and seal means for sealing said membrane to said stand-off section, wherein said membrane is adapted for conforming contact with said eye.

19. An apparatus for biasing a transducer assembly against an eye with a predetermined pressure not exceeding a threshold pressure which would cause deformation of the eye, comprising:
   an annular shaped transducer having a contact surface to matingly engage said eye;
   an inner housing member concentrically attached to said transducer and having a rear portion and a front portion, said front portion being greater in diameter than said rear portion and being provided with a tip section having a bore extending therethrough;
   a fixation light mounted concentrically within said tip section of said inner housing member at a rear end of said bore extending through said tip section, said bore extending outwards through a center of said annular shaped transducer;
   first lead means for transmission of electrical signals and connected to said fixation light and extending rearward through a center bore in said inner housing and exiting a rear portion of said inner housing;
   second lead means for transmission of electrical signals and connected to said transducer and extending rearward through said center bore in said inner housing and exiting said rear portion of said inner housing;
   an outer housing into which said inner housing is at least partially concentrically insertable, said outer housing having a front portion and a rear portion;
   bushing means for providing a low friction interface between said inner and outer housings and upon which said inner housing is slidably insertable into said outer housing, said bushing means being provided between said concentric inner and outer housings;
   means for limiting the movement of said inner housing relative to said outer housing between said extended position and said retracted position; and
   spring means for biasing said inner housing into said extended position with respect to said outer housing, said inner housing being positionable between said extended and retracted positions, said spring means having a spring constant which is the same in the retracted and extended position of the spring, and being positioned with respect to said limiting means such that the pressure applied by said transducer to said eye does not exceed said threshold pressure which would cause deformation of said eye.

20. The apparatus of claim 19 wherein said bushing means comprises a plurality of linear ball bushings.

21. The apparatus of claim 20 wherein said bushing means is attached to an inner surface of said outer housing.

22. The apparatus of claim 19 wherein said limiting means is adjustably removably attached to said outer housing so as to permit removal of said spring means and also to permit selection and adjustment of a preload force.

23. In a diagnostic device for measuring distances between anatomical structures of the type having a transducer assembly for contacting an anatomical surface, a transducer holding means for holding the transducer, lead means connected to said transducer for transmission of electrical signals, the improvement which comprises biasing means and second holding means, said transducer holding means being insertable into said second holding means and movable therein between an extended position and a retracted position, said biasing means being located between said second holding means and said transducer holding means such that said transducer holding means is biased in said extended position at rest and at least partially in said retracted position upon forceful engagement of said device with an eye, said biasing means providing biasing forces less than that which would cause deformation of said eye.

24. The diagnostic device of claim 23 further comprising means for limiting travel of said transducer holding means with respect to said second holding means, such travel being limited between said extending position and said retracted position.

25. The diagnostic device of claim 24 wherein said biasing means comprises a spring, said spring having associated therewith a spring constant, said spring constant being essentially the same in said extended position and in said retracted position.

26. The diagnostic device of claim 25 wherein said means for limiting travel comprises an end stop attached to said transducer holding means, said end stop contacting a first end of said spring.

27. The diagnostic device of claim 26 wherein said means for limiting travel further comprises an end plug attached to said second holding means, said end plug contacting a second end of said spring.

28. The diagnostic device of claim 27 wherein said end plug is removably attached to said second holding means so as to permit removal or replacement of said spring.

29. The diagnostic device of claim 28 further comprising a plurality of bushings attached to an inner surface of said second holding means, said bushings maintaining said inserted transducer holding means in a concentric relationship with said second holding means and also providing a low friction interface between said transducer holding means and said second holding means.

30. The diagnostic device of claim 29 wherein said bushings comprise linear ball bushings.

31. The diagnostic device of claim 23 further comprising a water stand-off attached to said front portion of said transducer holding means.

32. The diagnostic device of claim 31 wherein said water stand-off comprises a stand-off section, a membrane and seal means for sealing said membrane to said stand-off section, wherein said membrane is adapted for conforming contact with said eye.

33. A hand held apparatus for uniformly biasing a transducer against a human eye comprising:
 (a) an outer housing adapted to be hand held;
 (b) an inner housing slidably insertable into said outer housing and movable between an extended position for contact with said eye and a retracted position with respect to said outer housing for protective storage thereof;
 (c) spring means for biasing said inner housing into said extended position, said spring means having associated therewith a spring constant, said spring constant being essentially the same in said extended position and in said retracted position; and
 (d) means for limiting travel of said inner housing between said extended position and said retracted position including:
  (i) an end stop attached to said inner housing for contacting a first end of said spring means; and
  (ii) an end plug attached to said outer housing or contacting a second end of said spring means;
  (iii) wherein said end plug is adjustably removably attached to said outer housing so as to permit removal or replacement of sad spring means and selection and adjustment of a preload force; and
 (e) means for holding a transducer, said holding means and said transducer being provided on a front portion of said inner housing for engaging said eye when said inner housing is in said extended position; said spring means adapted to provide reduced biasing forces when said eye is contacted to avoid applanation thereof.

34. The apparatus of claim 33 further comprising illumination means concentrically mounted within said front portion of said inner housing rearward of said holding means and viewable by said eye.

35. The apparatus of claim 34 further comprising a curved contact member attached to said transducer for conforming contact with said eye.

36. The apparatus of claim 35 wherein said curved contact member and said transducer are each provided with a concentric bore therethrough so as to enable said eye to view said illumination means.

37. The apparatus of claim 33 further comprising an echo ranging device electrically connected to said transducer for calculating intraocular distances.

38. The apparatus of claim 33 further comprising a plurality of bushings attached to an inner surface of said outer housing for maintaining said inserted inner housing in a concentric relationship with said outer housing and providing a low friction interface between said inner and outer housings.

39. The apparatus of claim 38 wherein said bushings comprise linear ball bushings.

40. The apparatus of claim 33 further comprising means to indicate when said transducer holding means is advanced beyond a predetermined point.

* * * * *